United States Patent
Manigel et al.

(10) Patent No.: US 10,821,256 B2
(45) Date of Patent: Nov. 3, 2020

(54) DEVICE FOR PROVIDING A BREATHING GAS FLOW ENRICHED WITH ANESTHETIC

(71) Applicant: Drägerwerk AG & Co. KGaA, Lübeck (DE)

(72) Inventors: Jürgen Manigel, Hamburg (DE); Uwe Bartels, Lübeck (DE); Ralf Heesch, Lübeck (DE); Norbert Wruck, Lübeck (DE); Klaus Radomski, Lübeck (DE); Ulf Pilz, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 310 days.

(21) Appl. No.: 15/426,370

(22) Filed: Feb. 7, 2017

(65) Prior Publication Data

US 2017/0224947 A1 Aug. 10, 2017

(30) Foreign Application Priority Data

Feb. 8, 2016 (DE) .......................... 10 2016 001 383

(51) Int. Cl.
*A61M 16/12* (2006.01)
*A61M 16/01* (2006.01)
(Continued)

(52) U.S. Cl.
CPC ............ *A61M 16/12* (2013.01); *A61M 16/01* (2013.01); *A61M 16/104* (2013.01); *A61M 16/18* (2013.01);
(Continued)

(58) Field of Classification Search
CPC .... A61M 16/105; A61M 16/12; A61M 16/01; A61M 16/18; A61M 16/202; A61M 16/203; A61M 16/204; A61M 2016/1035
See application file for complete search history.

(56) References Cited

U.S. PATENT DOCUMENTS 4,605,034 A * 8/1986 Urushida ............ A61M 16/104
137/607
4,798,689 A * 1/1989 Heim ..................... A61M 16/18
128/203.14
(Continued)

FOREIGN PATENT DOCUMENTS

CN 101829386 A 9/2010
CN 102210898 A 10/2011
(Continued)

*Primary Examiner* — Jason E Flick
*Assistant Examiner* — Tasnim Mehjabin Ahmed
(74) *Attorney, Agent, or Firm* — McGlew and Tuttle, P.C.

(57) ABSTRACT

A method and device, for enriching a gas flow with an anesthetic, include a gas mixer (1), with gas inlets (2a, 2b) and one or more gas outlets (3a, 3b), and an anesthetic dispenser (4) connected to the one or more gas outlets. The anesthetic dispenser at least partially enriches the gas flow to provide a breathing gas flow enriched with anesthetic at a patient connector (5). A control valve (7a) is arranged fluidically in series with the anesthetic dispenser (4). The gas outlet is connected to the patient connector (5) via a gas channel (8), arranged fluidically parallel to the anesthetic dispenser (4) and in which at least another control valve (7b) is arranged. A control unit (6) actuates at least one control valve as a function of a desired value for an anesthetic concentration in the breathing gas flow to change anesthetic concentration at the patient connector (5).

18 Claims, 4 Drawing Sheets

(51) Int. Cl.
  *A61M 16/20* (2006.01)
  *A61M 16/10* (2006.01)
  *A61M 16/18* (2006.01)
  *A61M 16/00* (2006.01)

(52) U.S. Cl.
  CPC ... *A61M 16/202* (2014.02); *A61M 2016/0033* (2013.01); *A61M 2016/1025* (2013.01); *A61M 2016/1035* (2013.01); *A61M 2205/3331* (2013.01)

(56) References Cited

U.S. PATENT DOCUMENTS

| | | | | |
|---|---|---|---|---|
| 5,546,931 A * | 8/1996 | Rusz | ............ | A61M 16/18 128/203.12 |
| 5,957,129 A * | 9/1999 | Tham | ............ | A61M 16/104 128/204.22 |
| 5,967,141 A * | 10/1999 | Heinonen | ............ | A61M 16/18 128/203.12 |
| 2011/0000488 A1 * | 1/2011 | Blomberg | ............ | A61M 16/01 128/203.14 |

FOREIGN PATENT DOCUMENTS

| | | | |
|---|---|---|---|
| CN | 102355921 A | 2/2012 | |
| CN | 102872517 A | 1/2013 | |
| DE | 37 02 136 A1 | 8/1988 | |
| DE | 698 27 997 T2 | 12/2005 | |
| DE | 10 2005 012 340 B3 | 5/2006 | |
| EP | 0 545 567 A1 | 6/1993 | |
| EP | 0 545 567 B2 | 9/1999 | |
| WO | 2004/091708 A2 | 10/2004 | |

\* cited by examiner

DEVICE FOR PROVIDING A BREATHING GAS FLOW ENRICHED WITH ANESTHETIC

CROSS REFERENCE TO RELATED APPLICATIONS

This application claims the benefit of priority under 35 U.S.C. § 119 of German Application 10 2016 001383.4 filed Feb. 8, 2016, the entire contents of which are incorporated herein by reference.

FIELD OF THE INVENTION

The present invention pertains to a device for providing a breathing gas flow enriched with anesthetic at a patient connector. A gas mixer is provided here, which has at least two gas inlets, via which at least two different gases can be fed to the gas mixer. Further, a carrier gas-dependent anesthetic dispenser, which adds a volatile anesthetic to a gas flow, so that a breathing gas flow enriched with anesthetic as needed can finally be fed to the patient via the patient connector, is arranged fluidically downstream of the gas mixer.

BACKGROUND OF THE INVENTION

Many different anesthesia apparatuses, with which an anesthetic is fed into a breathing gas flow for a patient for the periodic anesthesia of the patient being ventilated by means of the anesthesia apparatus during this period, are known from the state of the art. Predominantly mechanically operating anesthetic dispensers continue to be used for enriching the breathing gas flow with volatile anesthetics. Such anesthetic dispensers operate, as a rule, according to the flow splitter principle and dispense the needed quantity of anesthetic into the fresh gas flow in a variably settable bypass. A breathing gas flow, which has the particular needed anesthetic concentration, is finally fed to the patient via the patient connector. These mechanically adjustable anesthetic dispensers are characterized by an especially high reliability, have been used for many years and therefore enjoy wide acceptance. It is, however, problematic in these devices that comparatively large thermal storage masses must be used to prevent the device from cooling when large evaporation mass flows are demanded, which would lead to an unacceptable drop in the vapor pressure and hence in the vapor output to be delivered. Due to the thermal storage masses needed, mechanically operating anesthetic dispensers are often comparatively heavy, which is, in turn, disadvantageous for handling.

It is necessary, precisely when using modern anesthesia methods in the field of the so-called minimal flow anesthesia, to reach the desired patient concentration by reducing the volume flow. If a technical arrangement with comparatively small thermal storage masses shall be used for this, considerable problems will, however, often occur with the use of the conventional methods in terms of the compensation of the cooling and general temperature effects, because large quantities of vapor are demanded in relevant applications.

If only the thermal storage masses are to be reduced despite the above-described problem to guarantee better handling of the anesthetic dispensers, the problem of excessive cooling would become even more acute. To solve the problem, electronically controlled anesthetic dispensers are generally used. Because of the comparatively high cost of the sensor system, temperature control as well as the actuation of the needed valves, no economically satisfactorily operating anesthetic dispensers have, however, hitherto been able to be provided.

An anesthetic dispenser, in which the flow of anesthetic is set as needed by means of a proportional valve operated in a controlled manner, is known from WO 2004/091708. The control is based on a fresh gas measurement and a closed control circuit on the liquid side. The anesthetic dispenser described here has an evaporating chamber, which is connected to the fresh gas flow, and a heating element, by which evaporation of the liquid anesthetic as needed shall be guaranteed, is provided within the evaporating chamber. However, the high cost of the sensor system and actuator mechanism needed is likewise a drawback of this fully electronically operating system.

Further, EP 0 545 567 B2 describes an anesthetic dispenser, in which an anesthetic evaporator is arranged fluidically parallel to a bypass channel surrounding same for a carrier gas. A carrier gas flow is formed here from at least two different gases and is finally branched off such that a first partial flow flows through the anesthetic evaporator and a second partial gas flow flows through the bypass channel. These partial flows are again mixed upstream of a patient connector. According to the technical solution described, the anesthetic concentration in the gas flow being fed to the patient is monitored and set to the needed value by the volume flow of the two partial flows being carried. The change in the volume flows is said to be changed here by means of a control circuit arranged in the flow channel containing the anesthetic evaporator and of a throttle in the bypass channel. Further, shut-off valves are provided in order to uncouple the anesthetic evaporator from the carrier gas flow as needed and thus to prevent gaseous anesthetic from reaching the carrier gas flow from the anesthetic evaporator, as soon as this is not needed.

SUMMARY OF THE INVENTION

Based on the solutions known from the state of the art for an anesthetic dispenser and the above-described problems, a basic object of the present invention is to provide an anesthetic dispenser, which can be actuated electronically and for which a very reliable evaporation technique with variable dispensing concentration can be used. A goal is to make it possible to use simple, lightweight evaporators with a low cost for the sensor system as well as for the actuator mechanism, in which evaporators the concentration with which volatile anesthetics are dispensed can be varied over time in the broadest possible range. Since anesthesiologists are accustomed, based on the prior-art, usually manually settable systems, to use such systems, anesthetic concentrations shall be able to be set in a range of 0.2% to 8% for the four essential volatile anesthetics, namely, halothane, enflurane, isoflurane as well as sevoflurane. The technical solution provided makes it possible, in particular, to dispense even large quantities of vapor in a reliable manner, on the one hand, and to have a low design effort and low costs for the control engineering for an anesthetic dispenser, on the other hand. The device to be proposed shall have especially only a small number of sensors as well as adjusting elements, so that a lightweight, failsafe, cost-effective and yet high-performance anesthetic dispensing is made possible. It is essential in this connection that an unacceptable thermal load on the volatile anesthetics being used be ruled out with certainty. At the same time, the safety-related and economic disadvantages of pressurized systems for anesthetic dispensing shall be avoided.

The present invention pertains to a device for enriching a gas flow with an anesthetic, which has a gas mixer with at least two gas inlets and at least one gas outlet and an anesthetic dispenser, which is indirectly or directly connected to the gas outlet in a gas-tight manner and which enriches the gas flow with an anesthetic at least at times such that a breathing gas flow enriched with anesthetic is provided at a patient connector. Further, a control unit is provided, which actuates a control valve, through which at least part of the gas flow flows, as a function of a desired value for an anesthetic concentration such that the anesthetic concentration is changed in the area of the patient connector in the direction of the desired value or to the desired value. The present invention is characterized in that a first control valve is arranged fluidically in series with the anesthetic dispenser, and that the at least one gas outlet of the gas mixer is connected to the patient connector via at least one gas channel, which is arranged fluidically parallel to the anesthetic dispenser and in which at least one second control valve is arranged.

The series connection of a gas mixer, preferably of an electronically controlled gas mixer, with at least one anesthetic dispenser, for example, with an anesthetic evaporator operating according to the principle of evaporation, is essential for the present invention, the needed quantity of an anesthetic being discharged from the anesthetic dispenser as needed by providing control valves actuated in a suitable manner and the anesthetic concentration being finally reduced by mixing to the value needed by the patient in the breathing gas flow of the patient. One of the control valves is arranged in at least one bypass channel, which fluidically bypasses the anesthetic evaporator and through which flows a carrier gas flow and One of the control valves is arranged in the at least one flow channel, in which the anesthetic dispenser is provided, on the other hand. It is essential for the technical embodiment that the control valves can be actuated independently from one another and the volume flow through them can also be reduced to zero value, i.e., 0 m$^3$/sec, so that at least one of the control valves is closed now as needed.

The mixing of the anesthetic concentration to the needed value takes place by means of an anesthetic-free gas flow or a gas flow having at least only a lower anesthetic concentration, which gas flow flows out of the gas mixer or another anesthetic dispenser, flows past the anesthetic dispenser and is finally mixed in a mixing point with the gas flow enriched with anesthetic, so that a breathing gas flow with the necessary anesthetic concentration is provided at the patient connector. The at least one flow channel, in which anesthetic-free gas flows as the carrier gas from the gas outlet of the gas mixer to the patient connector, without flowing through the at least one anesthetic dispenser, will hereinafter also be called bypass channel. It is conceivable, in principle, in this connection that the carrier gas being used is a gas, a gas mixture or a mixture of at least one gas with air.

It is generally conceivable that different gases are fed to the gas mixer, especially from a hospital gas supply system, and these leave the gas mixer as part of a gas mixture and/or in the original pure form via gas outlets provided in a corresponding number. The control unit likewise provided ensures that the at least one control valve, through which gas flows, is actuated such that the anesthetic concentration in the breathing gas flow at the patient connector is changed in the direction of a preset desired value for the anesthetic concentration or is set at least at a value close to this value. To guarantee such a control of the anesthetic concentration, at least one sensor is provided, preferably in the area of the patient connector, with which the anesthetic concentration of the breathing gas flow is detected and the detected value is sent to the control unit. According to a special variant of the present invention, a sensor is provided for determining an anesthetic concentration in the gas flow behind the anesthetic dispenser, for example, in the gas channel arranged between the anesthetic evaporator and the mixing point, at which a gas flow enriched with anesthetic is mixed with a gas flow not enriched with anesthetic. The values determined with this sensor are sent to a central control and analysis unit, which determines at first the volume flow as well as the anesthetic concentration of the gas flow being fed to the patient on the basis of the determined anesthetic concentration and the volume flows of the gas flows flowing through the anesthetic dispenser and/or at least one gas channel arranged parallel to the anesthetic dispenser. If necessary, at least one control signal is subsequently generated for actuating a control valve on the basis of these determined values and desired values preset by the user, so that the volume flow of the carrier gas flow flowing through the anesthetic evaporator and/or a bypass channel arranged parallel thereto is set.

By varying the volume flows of the gas flows flowing through the anesthetic dispenser as well as flowing around the anesthetic dispenser in the bypass channel, both the volume flow and the anesthetic concentration of the breathing gas flow can be varied in a comparatively wide range. In particular, a precise minimal flow anesthesia can be achieved in a comparatively simple manner. It is likewise possible to dispense large quantities of anesthetic, because the risk of unacceptable cooling of the anesthetic dispenser can be effectively counteracted by adapting the volume flow.

According to a special embodiment of the present invention, a sensor is provided for detecting the content or concentration of oxygen, laughing gas or carbon dioxide in a gas flow especially in the area of the gas mixer, of the bypass channel, of a dispensing area, especially evaporation area of the anesthetic dispenser and/or in the area of the patient connector. The corresponding gas concentration is preferably measured and the measured value is sent to an analysis unit, which compares the measured value with a desired or limit value. Based on this comparison, the control unit preferably generates a control signal, which initiates the needed adaptation of the content or concentration of the respective, at least one gas in the gas flow. According to a very special embodiment, the control unit is configured such that the control unit generates a control signal as needed for a control valve arranged in an oxygen line, so that the oxygen concentration in the gas flow is changed, especially increased, by adding oxygen-containing gas.

Provisions are made in another embodiment of the present invention for a mixing point, at which at least two gases flowing in from different gas inlets are mixed, to be arranged in the direction of flow between at least two gas inlets of the gas mixer and the anesthetic dispenser. It is conceivable in this connection to connect the gas mixer provided according to the present invention with the downstream anesthetic dispenser to the gas supply system of a hospital, so that different gases, especially oxygen, laughing gas and compressed air, are provided for the gas mixer at a pressure level intended especially for this purpose via separate gas lines. The corresponding lines of the hospital gas supply system are connected to the gas ports of the gas mixer, which are provided for this purpose. The control unit is configured in this case such that at least one control valve arranged downstream of the gas ports in the flow direction is actuated such that the corresponding volume flow of the gases being delivered through the individual lines can be set specifically and as needed to the needed value. At least two gases are mixed in the gas mixer and/or at the mixing point between the gas mixer and the anesthetic dispenser in the direction of flow and one of the gases being fed via the gas ports or a mixture of at least two of these gases is subsequently enriched with an anesthetic. The corresponding enrichment with anesthetic takes place in the anesthetic dispenser, through which a gas flow flows, and in which the gas flow is enriched with the anesthetic provided herefor preferably according to the evaporation principle. The gas or gases leaving the gas mixer, which flow through the anesthetic dispenser for enrichment with anesthetic depending on the request by the operator, are merged according to a special variant of the present invention at a point located fluidically downstream of the anesthetic dispenser, so that a gas mixture enriched with anesthetic is fed from this point to the patient connector via a provided line.

According to the above-described embodiment, it is conceivable, in principle, that at least two gas flows, at least one of which could contain an anesthetic, are mixed in upstream of the patient connector in the direction of flow, and that this gas mixture is fed to the patient connector. According to a special alternative, it is conceivable that a corresponding mixing takes place in the area of the patient connector or the patient connector has at least two ports upstream, via which gas flows possessing different properties, especially having different compositions, are fed to the patient connector.

The anesthetic dispenser is arranged according to the present invention fluidically parallel to at least one gas channel, also called bypass channel, in which an at least nearly anesthetic-free carrier gas flow flows. It is conceivable in this connection that the gas flow leaving the gas mixer is split such that a first partial flow flows through the anesthetic dispenser while a second partial flow flows parallel around the anesthetic dispenser. The first partial flow enriched with anesthetic as well as the second partial flow are preferably merged again at a mixing point located downstream of the anesthetic dispenser before these are fed as a global gas flow to the patient connector. The control unit is configured in this case such that the control valve arranged in the bypass channel as well as that arranged in the flow channel with the anesthetic dispenser are actuated such that an anesthetic concentration that corresponds to a desired value set by the user for the anesthetic concentration is reached in the gas flow at the mixing point. Once again, it is advantageous in this connection if a control valve, for example, in the form of a three-way valve, by which the gas flow is specifically split into a first partial flow as well as a second partial flow, is provided in the area of the gas channel, especially between a gas outlet of the gas mixer and the branch to the anesthetic dispenser. According to a special embodiment of the invention, the control valve arranged in the bypass channel is a proportional valve which acts as a pressure-controlled valve rather than as a flow-controlled valve. Thus this proportional valve is more or less an overflow-valve respectively a pressure relief valve. With this configuration, as the flow through the anesthetic dispenser is small compared to the total fresh gas flow, a small gas flow always passes through this proportional valve. According to another embodiment, the flow in the bypass channel is measured and the measured value is transmitted to the control unit.

It is conceivable according to a special variant that more than two control valves are arranged in different gas channels downstream of the gas inlets of the gas mixture, especially of the gas outlets. It is preferably conceivable in this connection that a first control valve is arranged between a first gas outlet of the gas mixer and the anesthetic dispenser and a respective second control valve and a third control valve are arranged in the flow direction downstream of at least one second gas outlet of the gas mixer, e.g., one or more gas outlets, which are connected each to the patient connector via a respective bypass channel. The control unit preferably controls the control valves such that a global breathing gas flow fed to the patient connector corresponds to the sum of the first volume flow and of an at least one second volume flow.

A mechanical throttling device is arranged according to a special variant of the present invention in at least one flow path between a gas outlet of the gas mixer and the patient connector. The at least one throttling device is preferably configured such that the pressure losses caused by the throttling device are coordinated with the pressure losses occurring during the flow through the anesthetic dispenser, especially in order to compensate these.

The volume flow ratio between the individual flow channels, i.e., especially between at least one first gas channel, in which an anesthetic dispenser is arranged, and a second gas channel, in which no anesthetic dispenser is provided, can be set in a specific manner by means of a mechanical throttling device thus provided, which preferably has a settable, especially automatically settable configuration.

According to a special embodiment, special throttle valves make it possible to embody fixed-flow valves or on-off valves. For example, splitting according to the desired value as well as global flow according to the desired value are generated by means of a diaphragm through which supercritical flow takes place and by means of cycling.

A special advantage of the present invention, which invention is based on a series connection of a gas mixer and a specific control of different gas flows, is above all that an anesthetic concentration can be set in a breathing gas flow to be made available to the patient to the necessary value in a comparatively simple manner. If a plurality of different gases are fed to the gas mixer via the gas inlets, the control valves actuated in a specific manner make it possible not to use individual gases for providing a breathing gas flow and to provide certain gases or gas mixtures in a specific manner as well as to vary the individual volume flows in a comparatively wide range. Highly precise anesthetic dispensing is possible in this manner for large as well as comparatively small volume flows alike.

Wide ranges of mixing ratios can be made possible in an advantageous manner with a type of pulse width modulation of the volume flows, the pulse width modulation being effected by means of valves actuated in a timed manner, which are moved from an open position into a closed position in a specific manner. Short pulses with longer pauses make it possible to dispense very small volume flows in an especially preferred manner.

In addition to a device for providing a breathing gas flow enriched with anesthetic for a patient to be anesthetized, the present invention pertains, furthermore, to a method for generating a gas flow enriched with anesthetic. A volume flow of a first gas as well as a volume flow of a second gas are provided according to the present invention and at least one anesthetic is added to a carrier gas flow formed from a first and/or second gas by means of an anesthetic dispenser as a function of a desired value for the anesthetic concentration of a breathing gas flow for the patient. The method of the present invention is characterized in that, taking into account the desired value for the anesthetic concentration, the volume flow of the first gas and/or the volume flow of the second gas are changed. A breathing gas flow containing an anesthetic is preferably provided by removing gas flows via at least two gas outlets of the gas mixer, but at least not all of these gas flows are sent to an anesthetic dispenser and are not enriched with anesthetic there. Rather, at least one gas flow flowing out of the gas mixer is enriched with anesthetic in the anesthetic dispenser and is finally mixed, upstream of the patient connector, with a gas, to which no anesthetic or only a comparatively small quantity of anesthetic had been added, such as to obtain the desired value of the anesthetic concentration in the breathing gas flow.

A comparatively simple method is thus proposed, especially a method that makes do without the great expense of sensors and actuating mechanisms. It is essential for the method according to the present invention that a gas mixer is combined with an anesthetic dispenser for anesthetics and a gas or a mixture of a plurality of gases can thus be enriched with an anesthetic in a specific manner and made available to a patient connector. Provisions are preferably made for the anesthetic to be added to a mixture of the first gas and the at least one second gas.

The enrichment of a gas flow in the anesthetic dispenser preferably takes place according to the evaporation principle, with at least one partial flow of a gas flow flowing advantageously through the anesthetic dispenser according to the flow splitter principle. Provisions are therefore made according to a special variant of the present invention for providing a bypass channel connected fluidically parallel to the gas channel with the anesthetic dispenser, in which bypass channel the gas flow is not enriched with an anesthetic. A first partial gas flow and at least one second partial gas flow, of which only the first partial gas flow is enriched with an anesthetic, while the second partial gas flow flows by the anesthetic dispenser, are provided in the gas mixer or downstream of the gas mixer in the flow direction.

The two partial gas flows are again merged at a mixing point located downstream of the anesthetic dispenser in the flow direction, so that a global gas flow enriched with anesthetic is generated. The enrichment of the first partial gas flow is carried out such that the global gas flow has an anesthetic concentration that corresponds to a value entered as a desired value for the anesthetic concentration.

Furthermore, it is conceivable to feed this global gas flow enriched with anesthetic to a patient connector or else to mix this with at least one additional gas as needed.

Provisions are made according to a very special variant of the present invention for a global volume flow, which is composed of at least two partial volume flows of gases or gas mixtures flowing out via the gas outlets of the gas mixer, to be set to a value of 0.1 L/min to 20 L/min. The different volume flows, which are fed to the gas mixer, are especially preferably set already such that a global volume flow formed from these different volume flows assumes the value that also corresponds to the breathing gas volume flow with which the patient shall be supplied.

The present invention will be explained in more detail below without limitation of the general inventive idea on the basis of special exemplary embodiments with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
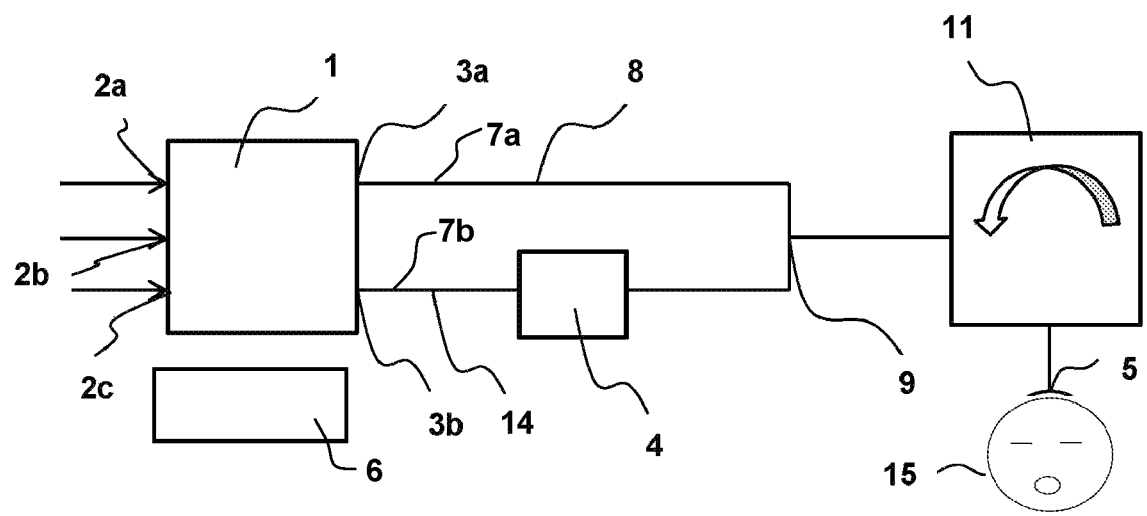
FIG. 1 is a schematic view showing a flow diagram with a controlled gas mixer, which is connected to a mixing point connected to a patient connector via a gas channel, in which an anesthetic dispenser is provided, and via a bypass channel arranged fluidically parallel thereto.

Referring to the drawings, FIG. 1 shows a flow diagram of a device for providing a gas flow, which is enriched with an anesthetic, for anesthetizing a patient 15. The gas flow enriched with anesthetic is fed to a breathing system 11, to which the patient 15 is connected. A so-called Y-piece, at which a gas channel is provided on the patient side for feeding and removing breathing gas, while an inspiratory gas channel as well as a separate expiratory gas channel are provided on the side facing away from the patient, is usually provided for this as a patient connector in the area of the patient. A gas flow enriched with anesthetic is fed to the Y-piece and hence to the patient via the inspiratory gas channel, while the breathing gas exhaled by the patient is removed via the expiratory gas channel. Valves, which preset the flow direction in the breathing system and enable the patient to exhale the gas being exhaled, are provided in the breathing system.

To supply the patient 15 with a gas enriched with anesthetic, a device configured according to the present invention has a gas mixer 1 with at least two gas inlets 2a, 2b and with at least one anesthetic dispenser 4, which is arranged downstream of the gas mixer 1 in the direction of flow. The anesthetic dispenser 4 is preferably configured as an anesthetic evaporator and adds a volatile anesthetic to a gas flow utilizing the evaporation principle. Halothane, enflurane, isoflurane or sevoflurane are optionally used as anesthetics. However, the present invention is not limited, in principle, to the use of the above-mentioned four anesthetics, but may also be used, in principle, with an anesthetic dispenser 4 that enriches a gas flow with a desflurane.

According to the exemplary embodiment shown in FIG. 1, the gas mixer 1 has three gas inlets 2a, 2b, 2c, which are connected to corresponding gas lines of a hospital gas supply system. Oxygen, compressed air as well as laughing gas ($N_2O$) are fed to the gas mixer 1, via the three gas lines and via the gas inlets 2a, 2b, 2c. The gas mixer 1 shown has an electronic control, so that the three gases or two gases and compressed air are either mixed and/or set to the necessary value in relation to the respective volume flow for a carrier gas flow corresponding to the anesthesiologist's specifications. The volume flows of the partial carrier gas flows are set by means of control valves formed as part of the mixer 1. The control valves 7a and 7b may also be provided as valves in the gas channels 8, 14 and may be connected to a control unit 6 (the control valves 7a and 7b as part of the mixer 1 or in the channels 8, 14 is only indicated and the connection to the control unit 6 is not shown so as to not crowd FIGS. 1 and 2). In the example shown in FIG. 1, the controlled gas mixer 1 has two gas outlets 3a, 3b, via which the two partial carrier gas flows, which may controlled by control unit 6 to have the same composition and rates of flow or different compositions and volume rates of flow different compositions and volume rates of flow, flow out.

A first partial carrier gas flow is sent from the first gas outlet 3b to the anesthetic dispenser 4, enriched there with anesthetic and subsequently mixed at a mixing point 9 with the second partial carrier gas flow, which flows out of the second gas outlet 3a of the gas mixer 1. The value of the volume flow of the carrier gas flow again corresponds at the mixing point 9 to the sum of the individual partial carrier gas flows of different gases fed to the gas mixer 1 via the gas inlets 2a, 2b, 2c as well as of the two partial flows of gas mixtures flowing out via the two gas outlets 3a, 3b. The value of the volume flow at the mixing point 9 corresponds to the volume flow that the patient needs for the anesthesia.

Figure 2:
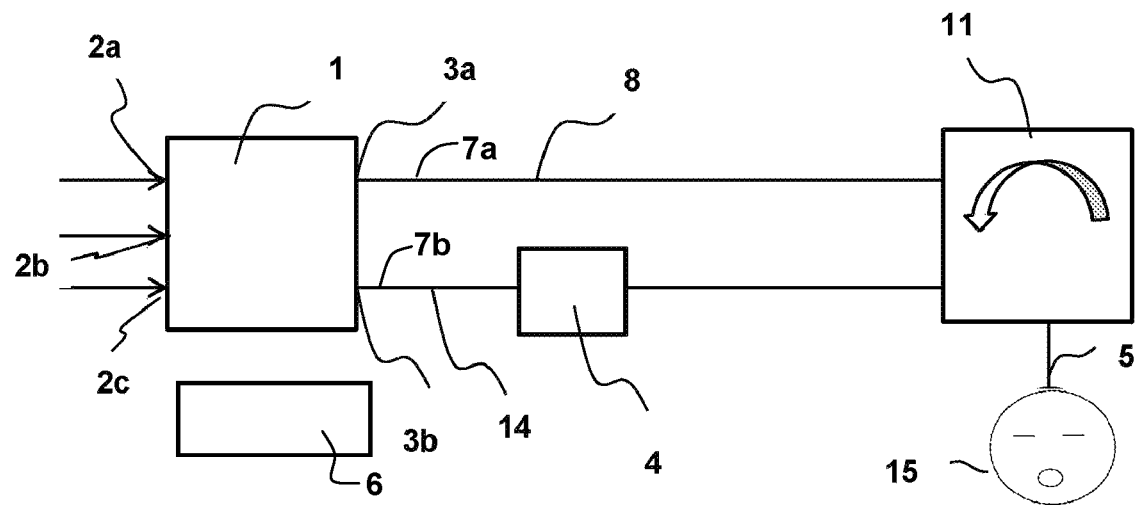
FIG. 2 is a schematic view showing a flow diagram with a controlled gas mixer, which is connected via a gas channel, in which an anesthetic dispenser is provided, and via a bypass channel arranged fluidically parallel thereto to a patient connector connected directly to the two channels.

FIG. 2 shows a special variant of the embodiment explained in connection with FIG. 1. Again, up to three different gases or two gases and air are fed to the gas mixer 1 and two partial carrier gas flows of a gas mixture 1 are removed from the gas mixer via two gas outlets 3a, 3b which may controlled to have the same composition and rates of flow or different compositions and volume rates of flow different compositions and volume rates of flow, flow out. The volume flows of the partial carrier gas flows are set by means of control valves formed as part of the mixer or the control valves 7a and 7b are provided as valves in the gas channels 8, 14. The volume flows are controlled with the valves 7a and 7b via the control unit 6. One of the two partial gas flows leaving the gas mixer 1 is fed, in turn, to an anesthetic dispenser 4 via a gas channel 14 and enriched with anesthetic there according to the evaporation principle. The other partial gas flow flows through a bypass channel 8 arranged fluidically parallel to the anesthetic dispenser 4 to the patient connector 5. However, contrary to the exemplary embodiment according to FIG. 1, the two partial gas flows are not mixed before they reach the breathing system, 11 with the patient connector 5, but the two partial gas flows are fed to the breathing system 11 with the patient connector 5 via separate gas channels 8, 14 or lines.

Figure 3:
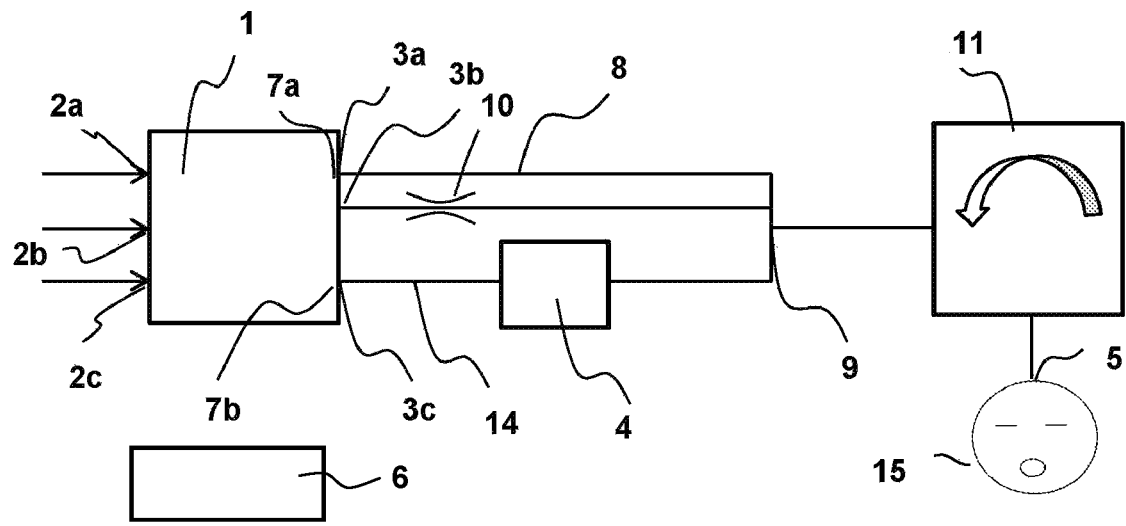
FIG. 3 is a schematic view showing a flow diagram with a controlled gas mixer, which is connected to a mixing point connected to a patient connector via a gas channel, in which an anesthetic dispenser is provided, via a bypass channel arranged fluidically parallel thereto and via a gas channel likewise connected parallel thereto with a throttle.

FIG. 3 shows a gas mixer, to which up to three different gases are again fed from a hospital gas supply system. The gases being fed are mixed as needed within the gas mixer 1 and/or the volume flow of at least one gas flowing through the gas mixer 1 is set as needed. Then, up to three partial gas flows, which may have the same composition and rates of flow or different compositions and volume rates of flow, flow out of the gas mixer 1 via three separate gas outlets 3a, 3b, and 3c.

A first of these partial gas flows is then fed to an anesthetic dispenser 4 configured as an anesthetic evaporator and arranged in the gas channel for enrichment with anesthetic, and the partial mixed gas flow enriched with anesthetic is sent to a mixing point 9. A second partial mixed gas flow is sent unchanged to the mixing point 9 via a bypass channel 8 arranged fluidically parallel to the anesthetic dispenser 4. A third partial mixed gas flow is sent to the mixing point 9 via a gas outlet 3c of the gas mixer 1, and via a throttling device 10, especially a mechanically adjustable throttle valve. The throttling device 10 causes a pressure drop (loss). The pressure loss caused by the throttling device 10 can be measured by a sensor to provide a flow measurement value. The flow measurement value of the flow through the gas outlet 3b may be provided to a control unit 6. The control unit 6 may then set the gas mixer 1 to adjust the flow out of the gas mixer 1 via the three separate gas outlets 3a, 3b, and 3c. The volume flows may also be controlled with the valves 7a and 7b via the control unit 6. The three partial mixed gas flows are mixed at the mixing point 9 and fed as a common gas flow to the breathing system 11 of the patient 15. The third partial mixed gas flow is throttled such that the pressure loss that is brought about by the anesthetic dispenser 4 is taken into account. A desired volume flow ratio can be set in this manner in a specific way between the three flow paths, which depends on the particular pressure losses in the three flow paths arranged in parallel. The volume flows of the partial carrier gas flows, which flow through the other two gas channels, one of these channels being a bypass channel 8, through which the flow is in parallel to the flow in the anesthetic dispenser 4, are set by means of control valves 7a, 7b, formed as part of the mixer 1, which are adjusted by means of a control unit 6 as a function of the desired global volume flow and the anesthetic concentration at the mixing point 9.

Figure 4:
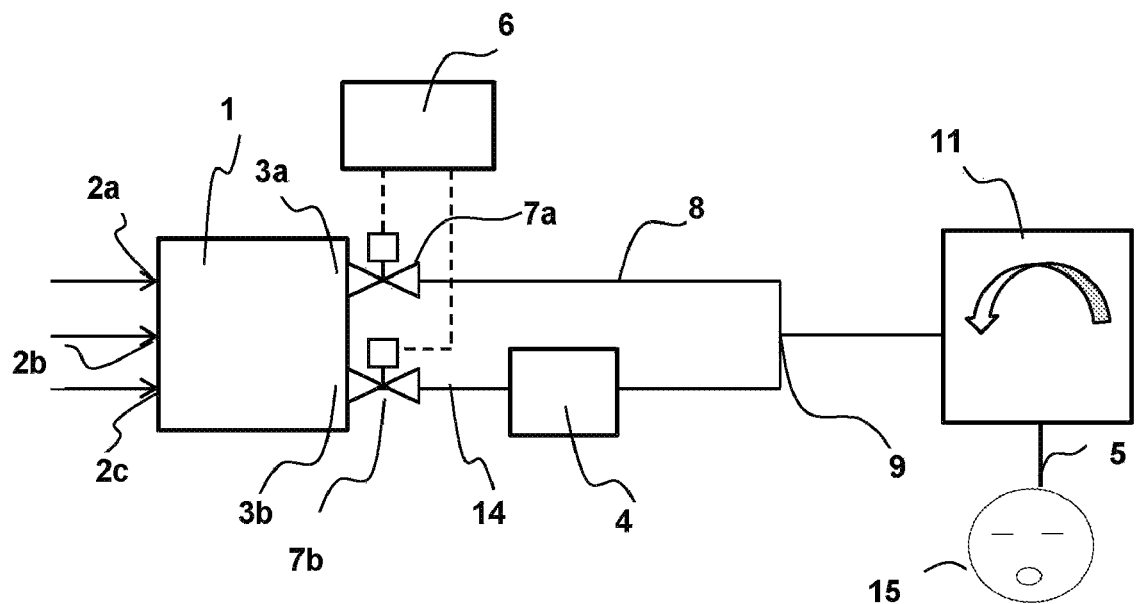
FIG. 4 is a schematic view showing a flow diagram with a gas mixer, which is connected to a mixing point connected to a patient connector via a gas channel, in which an anesthetic dispenser is provided, and via a bypass channel arranged fluidically parallel thereto, wherein a control valve each is arranged in the two channels downstream of the gas outlets of the gas mixer.

The exemplary embodiment shown in FIG. 4 corresponds to the exemplary embodiment according to FIG. 2, and control valves 7a, 7b, which are actuated by means of a control unit 6 as a function of the set desired value for an anesthetic concentration in the gas flow being fed to the patient 15, are additionally provided at the two gas outlets 3a, 3b of the gas mixer 1. The volume flow of the first and second partial gas flows leaving the gas mixer 1 can be set specifically to a needed value by the control valves 7a, 7b provided at the gas outlets 3a, 3b of the gas mixer 1. It is even conceivable, in principle, in this case to reduce at least one of the two partial gas flows to 0 (zero) at least at times if needed. The sum of the two partial gas flows leaving the gas mixer 1 will again correspond to the global volume flow of the gases fed to the gas mixer 1 as well as to the volume flow of the carrier gas flow being fed to the patient. The partial gas flows, which flow out of the gas mixer 1, may contain, as needed, a gas or air or else a mixture of at least two gases or of air and at least one gas.

An anesthetic dispenser 4, configured as an anesthetic evaporator, which enriches the first partial gas flow with a volatile anesthetic, is again provided in one gas channel 14 of the two gas channels 8, 14 arranged fluidically in parallel. After mixing the two partial gas flows at the mixing point 9, the anesthetic concentration corresponds at least approximately to the desired value set by the anesthesiologist for the anesthetic concentration in the breathing gas to be fed to the patient 15.

To make it possible to actuate the two control valves 7a, 7b in a specific manner, a concentration of the anesthetic is determined in the gas flow by means of a sensor behind the anesthetic dispenser 4 in the direction of flow, namely, in the area of the mixing point 9 of the breathing system 11 with the patient connector 5 and/or between the anesthetic dispenser 4 and the mixing point 9. If the determination of an anesthetic concentration is carried out in the area of the anesthetic dispenser 4 in the gas channel extending between the anesthetic dispenser 4 and the mixing point 9, the determined value is transmitted to a control and analysis unit 6, in which both the volume flow and the anesthetic concentration in the gas flow fed to the patient 15 are determined on the basis of the determined value and of the volume flows of the gas flows flowing through the anesthetic dispenser 4 and the bypass channel 8. Depending on a comparison between these actual values, especially the actual value for the anesthetic concentration in the gas flow sent to the patient 15, and the desired values preset by the user, the control and analysis unit 6 generates at least one control signal in case of a deviation for specifically actuating at least one of the control valves 7a, 7b in order to change the volume flow of the gas flow flowing through these valves 7a, 7b. If it is determined, for example, that the anesthetic concentration in the gas flow being sent to the patient 15 is too high, this concentration can be reduced by increasing the volume flow of the gas flow flowing through the bypass channel 8. If, in addition, the volume flow of the gas flow sent to the patient 15 is to be kept at a constant value or reduced, the volume flow of the carrier gas flow flowing through the anesthetic dispenser 4 must be reduced at the same time by specifically actuating the control valve 7b arranged in this flow channel 14. The determination of the volume flows needed in the respective gas channels is carried out in the control and analysis unit 6, taking into account the preset desired values for the volume flow and/or the anesthetic concentration in the carrier gas flow being sent to the patient 15.

Figure 5:
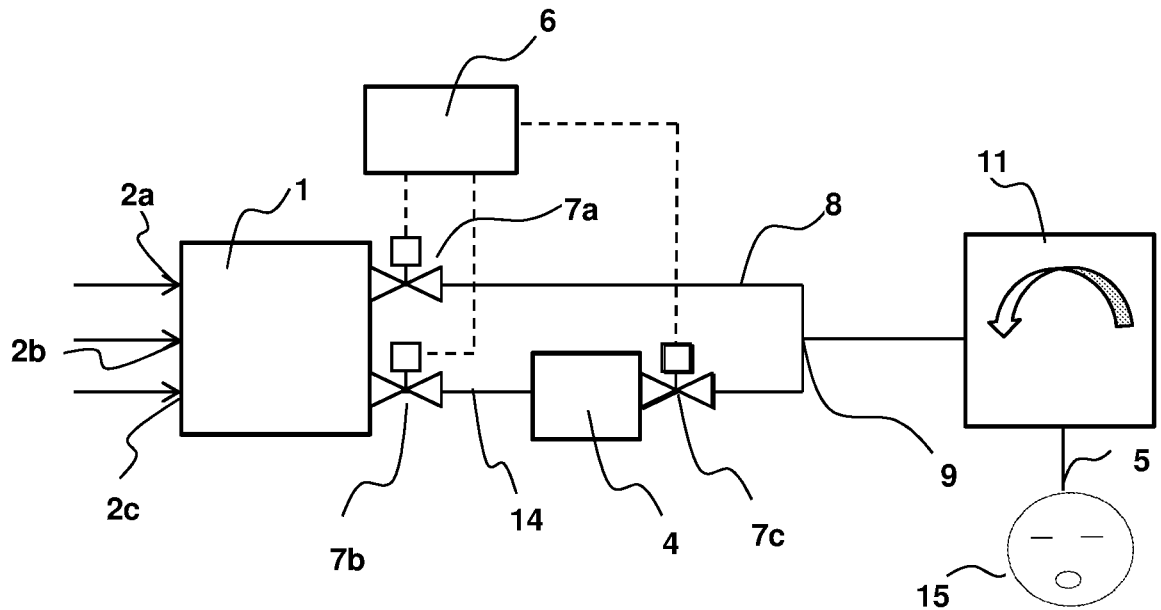
FIG. 5 is a schematic view showing a flow diagram with a gas mixer, which is connected to a mixing point connected to a patient connector via a gas channel, in which an anesthetic dispenser is provided, and via a bypass channel arranged fluidically parallel thereto, wherein a control valve each is provided in both channels downstream of the gas outlets of the gas mixer, on the one hand, and an additional control valve is provided downstream of the anesthetic dispenser.

The exemplary embodiment shown in FIG. 5 complements the exemplary embodiment according to FIG. 4 by an additional control valve 7c, which is arranged at the gas outlet of the anesthetic dispenser 4 configured as an anesthetic evaporator. The volume flow of the partial gas flow leaving the anesthetic dispenser 4 can once again be influenced by providing this additional control valve 7c, which is likewise actuated as a function of the anesthetic concentration value in the breathing gas. By providing two control valves 7b, 7c in this gas channel, especially the pressure loss prevailing on this flow path between the gas outlet 3b of the gas mixer and the mixing point 9 can be set precisely over an especially wide range. Likewise, more anesthetic can reliably be prevented from entering the mixing point 9 even though the control valve 7b directly behind the gas outlet 3b of the gas mixer 1 is already closed by providing the additional control valve 7c behind the anesthetic dispenser 4.

It is possible to set a ratio of the partial gas flows fed to the mixing point 9 in a specific manner by means of the three control valves 7a, 7b, 7c, two of which are provided at the two gas outlets 3a, 3b of the gas mixer and one at the gas outlet of the anesthetic dispenser 4, especially by changing the pressure losses in the two flow paths between the gas outlets 3a, 3b and the mixing point 9 in a specific manner.

Figure 6:
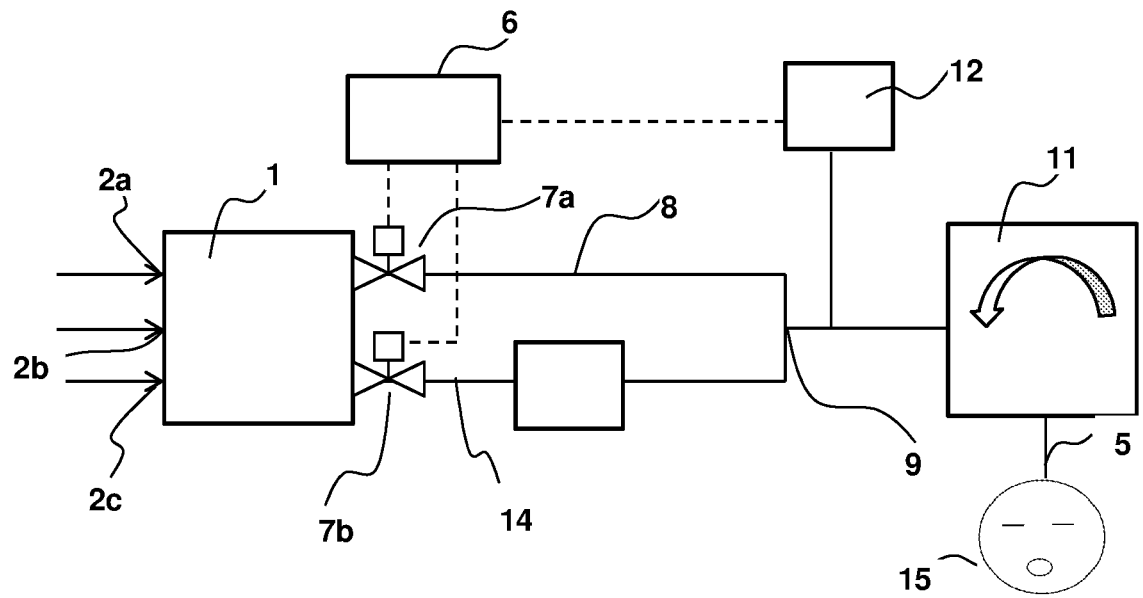
FIG. 6 is a schematic view showing a flow diagram with a gas mixer, which is connected to a mixing point connected to a patient connector via a gas channel, in which an anesthetic dispenser is provided, and via a bypass channel arranged fluidically parallel thereto, wherein a control valve each is arranged in both channels downstream of the gas outlets of the gas mixer and a gas-measuring module is arranged in the area of the patient connector.

The flow diagram according to FIG. 6 is complemented, compared to FIG. 5, by a gas-measuring module 12, which is connected, directly or indirectly via a gas line, to a gas channel, which is located in the direction of flow between the mixing point 9 and the breathing system 11 with the patient connector 5. The composition of the gas flowing through the gas channel in this area, on the one hand, and, on the other hand, the anesthetic concentration or, if more than one anesthetic is contained in the gas, also the anesthetic composition are detected by means of the gas-measuring module 12 shown in FIG. 6. Based on the measured values for the gas composition and/or the anesthetic concentration, the control unit 6 generates control signals for actuating the two control valves 7a, 7b arranged at the gas outlets 3a, 3b of the gas mixer 1, taking into account the desired values preset by the user. The control valves 7a, 7b are actuated such that the partial gas flows, of which only a first partial gas flow is enriched with anesthetic by the anesthetic dispenser 4, are split such that a value of the anesthetic concentration that corresponds to the stored or entered desired value becomes established at the mixing point 9 at least after a transition period.

Figure 7:
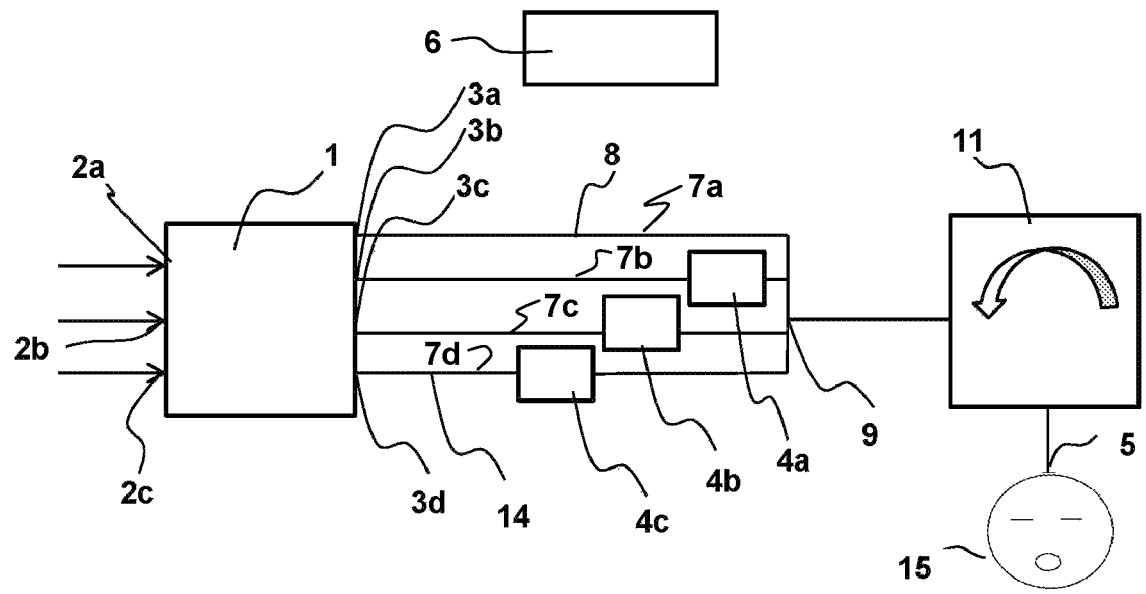
FIG. 7 is a schematic view showing a flow diagram with a controlled gas mixer, which is connected via four gas channels arranged fluidically in parallel to a mixing point connected to a patient connector, wherein an anesthetic dispenser each is provided in three of the four gas channels.

FIG. 7 shows a special embodiment of the present invention, in which oxygen, laughing gas, as well as compressed air, are again fed to the gas mixer 1, mixed in a suitable manner in the gas mixer 1 and/or provided as pure gas in the desired quantity and four partial gas flows, which contain each a gas or a mixture of at least two gases or of air and at least one gas, are removed via the four gas outlets 3a, 3b, 3c, 3d, which may be controlled to have the same composition and rates of flow, or different compositions and volume rates of flow, of the gas mixer 1. The four flow paths between the gas mixer 1 and mixing point 9 are again arranged fluidically parallel.

One of the four partial gas flows generated is delivered unchanged to the mixing point 9 via the bypass channel 8. The other partial gas flows are sent each to an anesthetic dispenser 4a, 4b, 4c, in which they are enriched with anesthetic as needed. It is conceivable in this connection that three different anesthetics, which are sent to the patient 15 corresponding to the state of the patient 15 or the current phase of the anesthesia, are contained in the three anesthetic dispensers 4a, 4b, 4c. The three partial gas flows, which flow through each a respective anesthetic dispenser 4 configured as an anesthetic evaporator, are mixed with the fourth partial gas flow at the mixing point 9. It is, of course, conceivable in this connection that not all of the three partial gas flows, which are fed to an anesthetic dispenser 4, are enriched with anesthetic, for example, because no anesthetic is present, at least at times, in one of the anesthetic dispensers 4, or because not all of the three anesthetic dispensers 4 arranged in parallel carry a gas flow. In this case as well, the gas mixer 1 is an electronically controlled gas mixer 1, especially that of an anesthesia apparatus, which brings about a splitting of the global gas flow fed to the gas mixer 1 into the needed partial flows.

Figure 8:
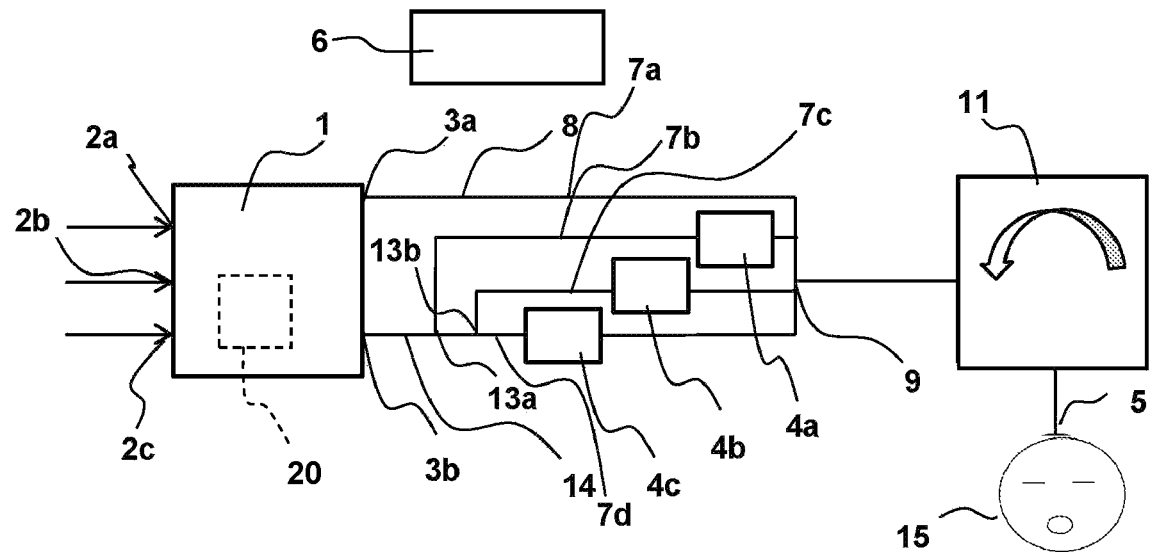
FIG. 8 is a schematic view showing a flow diagram with a controlled gas mixer, which is connected to a mixing point connected to a patient connector via two gas channels arranged fluidically in parallel, wherein one of the two gas channels branches off, in turn, into three gas channels arranged in parallel to one another, in which an anesthetic dispenser each is provided.

Finally, the exemplary embodiment according to FIG. 8 shows a device for enriching a gas flow with an anesthetic, whose gas mixer 1 has two gas outlets 3a, 3b, to which gas channels 8, 14 are connected, which are merged downstream at a mixing point 9. Two branching points 13a, 13b are provided in one 14 of the two gas channels 8, 14 leaving the gas mixer 1, so that this gas channel is split into three partial gas channels arranged fluidically parallel. An anesthetic dispenser 4a, 4b, 4c configured as an anesthetic evaporator is, in turn, provided in each of these three partial gas channels. The global gas flow is split into the partial gas flows flowing through the different gas channels by means of control valves 7a, 7b, 7c, 7d with this embodiment as well. The control valves 7a, 7b, 7c, 7d, located in the gas channels, are actuated by a control unit 6 as a function of an anesthetic concentration value of the gas flow to be fed to the patient. The connection of the control unit 6 to the control valves 7a, 7b, 7c, 7d, is omitted to not overcrowd FIG. 7. The magnitude of the respective volume flow depends on the value of the global volume flow, on the division into partial gas flows, which is brought about by the gas mixer 1, on the setting of the control valves 7a, 7b, 7c, 7d, as well as on the flow resistances of the individual flow paths.

It is again essential that the volume flows, which flow through the individual flow paths, are be such that a global volume flow as well as an anesthetic concentration of the gas flow that corresponds to the desired value set by the user, especially for the anesthetic concentration, are generated in the area of the mixing point 9, so that a gas flow conditioned according to the needs can be fed to the breathing system 11 of the patient.

A further embodiment according to the invention is provided as a variant of the embodiments discussed above. The further embodiment is particularly discussed with reference to FIG. 8. In the variation, at least one of the control valves (7a, 7b, 7c, 7d), arranged in the gas channel comprising the anesthetic dispenser 4 (or 4a, 4b, 4c), is controlled algorithmically based on at least one flow measurement in the gas mixer 1. The control algorithm of the control unit 6, uses an output from a flow measuring device 20, for measuring a gas flow, to control the setting of at least one of the control valves (7a, 7b, 7c, 7d) arranged in the gas channel. The connection of the control unit 6 to the control valves 7a, 7b, 7c, 7d, is omitted to not overcrowd FIG. 8. The flow measuring device 20 (shown in dashed line in FIG. 8 to indicate it is present in a variant of the embodiment of FIG. 8) is located inside and/or is a part of the gas mixer 1. The flow measuring device 20 may be a located inside and/or a part of the gas mixer 1 of one of the other embodiments of FIGS. 1-7. In the variations with the measuring device 20 in or a part of the gas mixer 1, a signal from the measuring device 20, indicating gas flow, is sent to the control unit 6. The control unit 6 then algorithmically controls, based on the output from a measuring device 20, the setting of at least one of the control valves (7a, 7b, 7c, 7d) arranged in the gas channel with the anesthetic dispenser 4 (4a, and/or 4b, and/or 4c).

While specific embodiments of the invention have been shown and described in detail to illustrate the application of the principles of the invention, it will be understood that the invention may be embodied otherwise without departing from such principles.

APPENDIX

1 Gas mixer
2 Gas inlet
  2a first gas inlet
  2b second gas inlet
  2c third gas inlet
3 Gas outlet
  3a first gas outlet
  3b second gas outlet
  3c third gas outlet
  3d fourth gas outlet
4 Anesthetic dispenser
  4a first anesthetic dispenser
  4b second anesthetic dispenser
  4c third anesthetic dispenser
5 Patient connector
6 Control unit
7 Control valve
  7a first control valve
  7b second control valve
  7c third control valve
8 Gas channel (bypass channel) arranged parallel to the anesthetic dispenser
9 Mixing point
10 Throttling device
11 Breathing system
12 Gas-measuring module
13 Branching point
  13a first branching point
  13b second branching point
14 Gas channel with anesthetic dispenser
15 Patient

What is claimed is:

1. A device for enriching a gas flow with an anesthetic, the device comprising:
a gas mixer comprising at least two gas inlets and at least one gas outlet;
an anesthetic dispenser;
a flow channel comprising a gas channel fluidically connecting the anesthetic dispenser to the at least one gas outlet, the anesthetic dispenser being configured to enrich an anesthetic dispenser gas flow with an anesthetic at least periodically to provide an enriched breathing gas flow, which is enriched with anesthetic;
a first control valve arranged fluidically in series with the anesthetic dispenser in the flow channel, the first control valve being configured to reduce volume flow through the first control valve to zero;
a patient connector fluidically connected to the gas channel;
another gas channel fluidically connecting the at least one gas outlet to the patient connector and arranged fluidically parallel to the anesthetic dispenser, said another gas channel forming a bypass channel flowing anesthetic-free gas from the gas outlet to the patient connector;
a second control valve arranged in the another gas channel, the second control valve being configured to reduce volume flow through the second control valve to zero, the first and second control valves being configured to be actuated independently of each other; and
a control unit configured to actuate the first control valve or the second flow valve or both the first control valve or the second flow valve as a function of a desired value for an anesthetic concentration in the breathing gas flow such that the anesthetic concentration is changed at the patient connector toward the desired value or to the desired value.

2. A device in accordance with claim 1, wherein the gas channel and the other gas channel form at least one mixing point at which gas flows are mixed upstream of the patient connector.

3. A device in accordance with claim 2, wherein:
the first control valve is arranged between one of the at least two gas inlets and the anesthetic dispenser for changing a first volume flow flowing through the first control valve;
the second control valve is arranged between one of the at least two gas inlets and the mixing point for changing a second volume flow flowing through the second control valve; and
the control unit actuates the first control valve and the second control valve such that a global carrier gas flow, fed to the patient connector, corresponds to the sum of the first and second volume flows.

4. A device in accordance with claim 3, wherein the at least two gas inlets are supplied with different gases.

5. A device in accordance with claim 1, wherein:
the at least one gas outlet comprises a first gas outlet and at least one second gas outlet; and
the gas channel connects the first gas outlet to a breathing system with the patient connector; and
the another gas channel connects the at least one second gas outlet to the breathing system with the patient connector.

6. A device in accordance with claim 1, further comprising a further gas channel, with a mechanical throttling device, fluidically connecting at least one of the at least two gas inlets and the patient connector.

7. A device in accordance with claim 1, wherein:
the control unit switches over at least one of the control valves in a cycle between an open position and a closed position; and
a time period during which the respective control valve is in a closed position is longer than a time period during which the control valve is in an open position.

8. A device in accordance with claim 1, wherein the gas mixer is part of an anesthesia apparatus capable of operating independently.

9. A device in accordance with claim 1, further comprising a flow measuring device for measuring at least one gas flow of the gas mixer, the flow measuring device being located inside the gas mixer or forming a part of the gas mixer or both located inside the gas mixer and forming a part of the gas mixer, wherein the first control valve, arranged fluidically in series with the anesthetic dispenser, is controlled algorithmically based on at least one flow measurement in the gas mixer.

10. A method for generating a gas flow enriched with anesthetic, the method comprising:
providing a device comprising:
a gas mixer comprising at least two gas inlets and at least one gas outlet;
an anesthetic dispenser;
a flow channel comprising a gas channel fluidically connecting the anesthetic dispenser to the at least one gas outlet, the anesthetic dispenser being configured to enrich an anesthetic dispenser gas flow with an anesthetic at least periodically to provide an enriched breathing gas flow, which is enriched with anesthetic;
a first control valve arranged fluidically in series with the anesthetic dispenser in the flow channel, the first control valve being configured to reduce volume flow through the first control valve to zero;
a patient connector fluidically connected to the gas channel;
another gas channel fluidically connecting the at least one gas outlet to the patient connector and arranged fluidically parallel to the anesthetic dispenser, said another gas channel forming a bypass channel flowing anesthetic-free gas from the gas outlet to the patient connector;
a second control valve arranged in the another gas channel, the second control valve being configured to reduce volume flow through the second control valve to zero, the first and second control valves being configured to be actuated independently of each other;
a control unit configured to actuate the first control valve or the second flow valve or both the first control valve or the second flow valve as a function of a desired value for an anesthetic concentration in the breathing gas flow such that the anesthetic concentration is changed at the patient connector toward the desired value or to the desired value;
providing a first volume flow of a first gas via the first control valve;
providing a second volume flow of a second gas via the second control valve;
forming a carrier gas flow from the first volume flow or from the second volume flow or from both the first volume flow and the second volume flow;
adding at least one anesthetic to the carrier gas flow with the anesthetic dispenser as a function of the desired value for the anesthetic concentration; and
changing the volume flow of the first gas and the volume flow of the second gas taking into account the desired value via the control unit.

11. A method in accordance with claim 10, wherein the second volume flow is set independently from the first volume flow to a value that is greater than or equal to zero.

12. A method in accordance with claim 10, wherein the anesthetic is added to a mixture of the first gas and the at least one second gas.

13. A method in accordance with claim 10, wherein the carrier gas flow is composed of the first volume flow and the second volume flow of the second gas and is set to a value of 0.1 L/min to 20 L/min.

14. A method in accordance with claim 10, wherein the anesthetic concentration is determined in a gas flow leaving the anesthetic dispenser before this gas flow is mixed with at least one additional gas flow.

15. A method in accordance with claim 14, wherein the first volume flow and the second volume flow are changed by taking into account the desired value and the anesthetic concentration in the gas flow leaving the anesthetic dispenser.

16. A device for enriching a gas flow with an anesthetic, the device comprising:
a gas mixer having a plurality of gas inlets and gas outlets, said gas mixer being configured to receive a plurality of different gases, said gas mixer being configured to selectively deliver a gas mixture of the plurality of different gases;
a first gas channel having one end connected to one of said gas outlets and another end connected to a mixing point;
an anesthetic dispenser arranged in said first gas channel between said gas outlet and said mixing point, said anesthetic dispenser being configured to enrich a gas flow in said first channel with an anesthetic;

a first control valve arranged in said first gas channel between said gas outlet and said anesthetic dispenser, said first control valve being configured to reduce volume flow through said first control valve to zero;

a second gas channel connected to another one of said gas outlets and said mixing point;

a second control valve arranged in said second gas channel between said gas outlet and said mixing point, said second control valve being \configured to reduce volume flow through said second control valve to zero, said first and second control valves being configured to be actuated independently of each other;

a patient connector connected to said mixing point, and one of arranged at, and downstream of, said mixing point;

a control unit configured to selectively activate one of said first control valve and said second control valve as a function of a desired value of the anesthetic from said to selectively change an anesthetic concentration at said patient connector to a desired value.

17. A device in accordance with claim 16, further comprising:

an anesthetic sensor arranged at, or between, said anesthetic dispenser and said patient connector, said anesthetic sensor measuring anesthetic concentration in a gas flow at, or downstream of, said anesthetic dispenser;

said control unit being configured to selectively activate said first control valve and said second control valve as a function of the anesthetic concentration measured by said anesthetic sensor.

18. A device in accordance with claim 16, wherein:
said anesthetic dispenser is an anesthetic vaporizer.

* * * * *